United States Patent [19]

Piesinger

[11] 4,432,367
[45] Feb. 21, 1984

[54] ELECTROCARDIOGRAPH RECEIVER

[76] Inventor: Gregory H. Piesinger, 6702 E. Cactus Rd., Scottsdale, Ariz. 85254

[21] Appl. No.: 354,373

[22] Filed: Mar. 3, 1982

[51] Int. Cl.$^3$ .............................................. A61B 5/04
[52] U.S. Cl. ................................................... 128/639
[58] Field of Search .............. 128/639, 644, 783, 798, 128/802, 803; 604/20

[56] References Cited

U.S. PATENT DOCUMENTS

| 542,508 | 7/1895 | Tuyl, Jr. ................................ 604/20 |
| 3,659,614 | 5/1972 | Jankelson ........................ 128/803 X |
| 3,826,245 | 7/1974 | Funfstuck ............................ 128/639 |
| 3,848,582 | 11/1974 | Milani et al. ......................... 128/639 |
| 4,014,323 | 3/1977 | Gilmer et al. ................... 128/639 X |
| 4,033,333 | 7/1977 | DeSalvo et al. ..................... 128/639 |

FOREIGN PATENT DOCUMENTS 198502  5/1976  U.S.S.R. .............................. 128/639

OTHER PUBLICATIONS

Takagi et al., "The Electrodes-Triangle", Am. Heart J., Sep. 1970, pp. 427-428.

Primary Examiner—Lee S. Cohen

[57] ABSTRACT

A single piece electrocardiograph receiver including a pair of electrodes having pieces of spongy porous material associated therewith and mounted at opposite ends of a handle so as to be in a fixedly spaced orientation. The spongy material absorbs a conductive material, such as water, and the receiver can then be pressed against the side of an animal in a heart spanning orientation to receive the electric impulses from the heart.

3 Claims, 1 Drawing Figure

U.S. Patent      Feb. 21, 1984      4,432,367
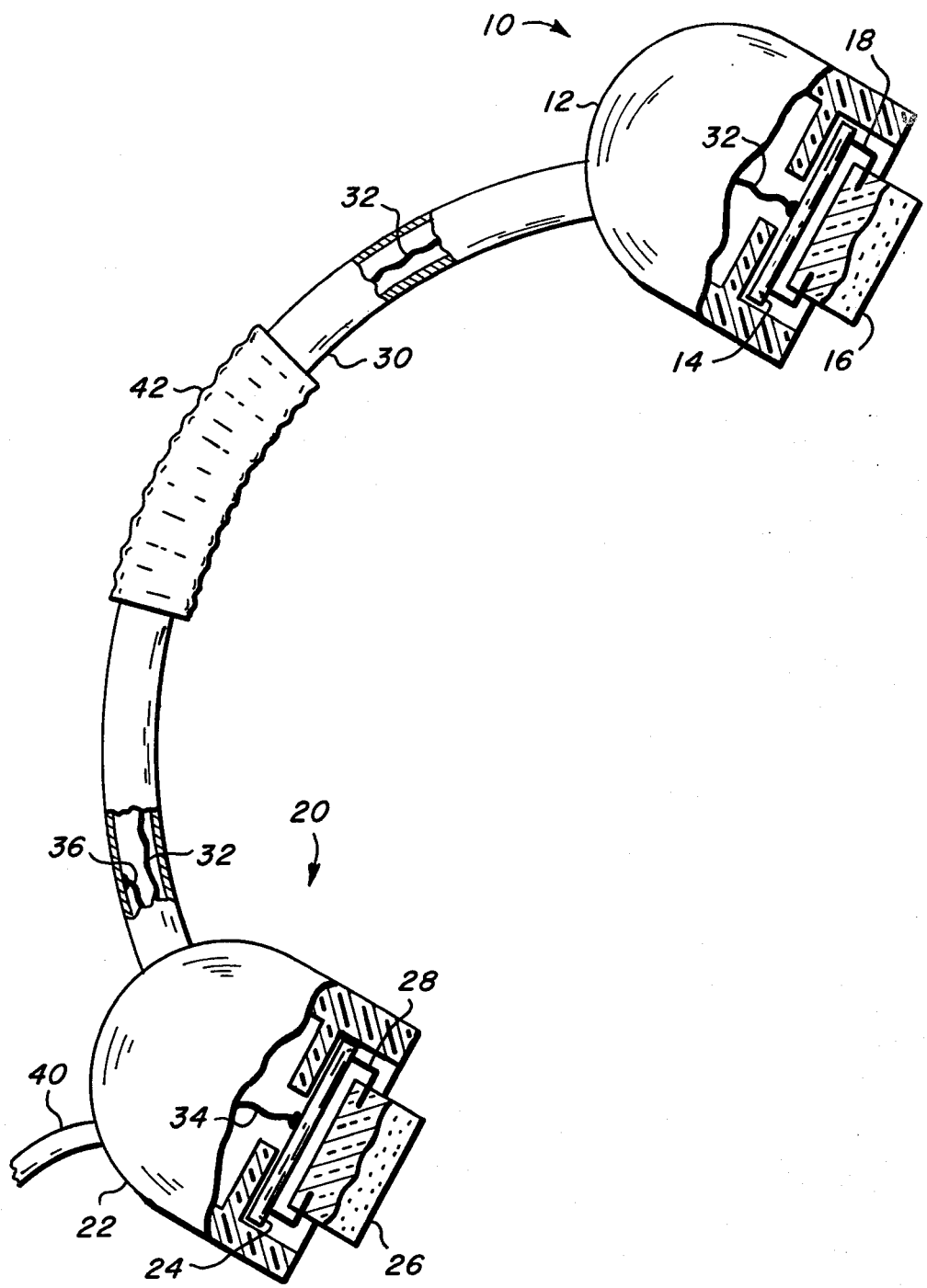

ELECTROCARDIOGRAPH RECEIVER

BACKGROUND OF THE INVENTION

Electrocardiogram voltages are normally obtained by taping two voltage pickup electrodes and a ground electrode to the patient. On animals, small patches of skin must be shaved free of hair, while on humans, clothing must be removed so that the electrodes can be attached on bare skin.

SUMMARY OF THE INVENTION

The present invention pertains to an electrocardiograph receiver formed in a single unit and including first and second electrodes each having associated therewith resilient porous material adapted to absorb an electrically conducting liquid. The electrodes are mounted at opposite ends of a handle which fixedly positions the electrodes in a heart spanning relationship. In a specific embodiment the handle may be connected as the ground of the electrocardiograph so that the operator has simply to wet the resilient porous material, press the receiver against the patient so as to span the heart and place the other hand on the patient on a patch of bare skin or damp hair or fur.

It is an object of the present invention to provide a new and improved electrocardiograph receiver.

It is a further object of the present invention to provide a new and improved electrocardiograph receiver formed in a single unit for greatly simplifying the process of obtaining electrocardiogram (ECG) voltages.

These and other objects of this invention will become apparent to those skilled in the art upon consideration of the accompanying specification, claims and drawing.

BRIEF DESCRIPTION OF THE DRAWING

The single FIGURE is a view inside elevation of an electrocardiograph receiver embodying the present invention, portions thereof removed and shown in section.

DESCRIPTION OF THE PREFERRED EMBODIMENT

Referring to the single Figure, the No. 10 generally designates a first electrode assembly including a housing 12, and electrode 14, and a piece of resilient porous material 16. A second electrode assembly, generally designated 20, includes a housing 22, and electrode 24, and a piece of resilient porous material 26. In this embodiment the housings 12 and 22 are molded from an electrically insulating material, such as plastic or the like. The housings 12 and 22 are formed in a generally bell shape to reduce the number of sharp corners and the possibility of injury thereon. The flat side of each of the bell shaped housings 12 and 22 has a cavity defined therein with the electrodes 14 and 24, respectively, fixedly mounted therein. The electrodes 14 and 24 are generally flat plates which can be affixed to the inner wall of the cavities formed in the housings 12 and 22. The electrodes 14 and 24 may be affixed in the cavities by any convenient means, such as screws, epoxy, molding in place, etc. With the electrodes 14 and 24 fixed in place within the cavities in the housings 12 and 22, respectively, a recess is defined for receiving the resilient absorbing material 16 and 26. While any resilient liquid absorbing material might be utilized for the pieces of material 16 and 26, pieces of sponge, or any of the man-made materials commonly referred to as sponge, are the most convenient because of the ease of obtaining and the nominal expense. The pieces of material 16 and 26 may be held in place by a variety of means but in the present embodiment a plurality of inwardly projecting fingers 18 and 28, respectively, are utilized. The fingers 18 and 28 are formed of a spring-like material which is attached to the electrodes 14 and 24, respectively, and projects into the material 16 and 26 to hold it fixedly adjacent the electrodes 14 and 24, respectively. In the present embodiment the electrodes 14 and 24 are formed of a stainless steel plate while the fingers 18 and 28 are formed of stainless steel wire to prevent any possible corrosion or the like. By forming the fingers 18 and 28 of a resilient wire material the material 16 and 26 can be periodically changed as it becomes worn or dirty.

The housings 12 and 22 are fixedly positioned in a spaced-apart relationship with respect to each other by means of an elongated tubular member 30. The tubular member 30 forms a handle and the housings 12 and 22 are affixed to the ends thereof by any covenient means. The tubular member 30 is formed slightly arcuately for ease of operation, as will become apparent presently. An insulated wire 32 extends through the tubular member 30 and is attached to the electrode 14 at one end thereof. A second insulated wire 34 is attached at one end to the electrode 24. In this embodiment the tubular member 30 is formed of a semi-flexible chrome plated copper tubing and a third insulated wire 36 is attached to the inner wall of the member 30. The 3 wires 32, 34, and 36 extend outwardly in a single 3 conductor lead wire 40 which is adapted to be attached to an electrocardiogram (not shown). A short section of rubber sleeve 42, optionally, may be provided in overlying relationship to a centrally located section of the tubular member 30. The rubber sleeve is provided for a non-slip hand grip to allow easier manipulation of the receiver, but the rubber section must be small enough (in this embodiment) to allow the operator to come in contact with the tubular member 30, for reasons that will become apparent presently.

In the operation of the receiver illustrated in FIG. 1, the sponges 16 and 26 are wetted by means of clear water or water with a slight amount of salt therein. The operator then grips the handle, tubular member 30 and rubber sleeve 42 (if present), and presses the receiver against the side of the patient, if the patient is, for example, a horse the receiver is pressed against the sides so that the electrode assemblies 10 and 20 span the heart, i.e., sponges 16 and 26 engage the body on opposite sides of the heart. The electrode assemblies are forced against the body, by pressing on the tubular member 30, so that good electrical contact is made through the hair (or clothes) of the patient without requiring shaving or disrobing. The moisture from the sponges 16 and 26 passes through the hair or clothing and provides a proper electrical contact with the electrodes 14 and 24. In the embodiment illustrated, the operator has one hand in contact with the electrically conducting tubular member 30 and simply places the other hand on a damp spot on the patient or on a piece of bare skin to complete a proper ground connection. It will of course be understood that this ground connection is simply for convenience and a great variety of other ground connections might be provided, such as another electrode assembly, etc.

Thus, an electrocardiogram receiver is disclosed which is simple to manufacture and very convenient to operate. In general, the receiver illustrated can be utilized in the field with literally no preparation of the patient, such as shaving, disrobing, etc. For example, if a portable electrocardiogram is provided, the present receiver can be utilized to inspect the hearts of horses immediately subsequent to a period of great exertion, such as a race or the like.

While I have shown and described a specific embodiment of this invention, further modifications and improvements will occur to those skilled in the art. I desire it to be understood, therefore, that this invention is not limited to the particular form shown and I intend in the appended claims to cover all modifications which do not depart from the spirit and scope of this invention.

I claim:

1. An electrocardigraph receiver for receiving electric impulses produced by the heart muscle of an animal, said receiver comprising:
    a first and second electrode means each including an electrode and resilient porous sponge means adapted to absorb an electrically conducting liquid and positioned for completing electrical contact between the associated electrode and an animal's body when the electrode means is pressed thereagainst, said electrode means each further including a housing having the associated electrode fixedly engaged therein with he porous means maintained in proximity to the electrode and extending externally of said housing for providing contact with the animal's body;
    means mechanically connecting said first and second electrode means and fixedly positioning said electrode means in spaced apart relationship a distance at least as great as the span of the animal's heart muscle, said mechanical means including an elongated, semi-flexible tubular member having a housing of each electrode means affixed to each end thereof and forming a handle for pressing said first and second electrode means against the body of the animal; and
    means for electrically coupling the electrodes of said electrode means to an electrocardiograph.

2. An electrocardiograph receiver as claimed in claim 1 wherein the means electrically coupling the electrodes includes insulated wire extending through the tubular member,
    the tubular member is formed with at least an external portion thereof being electrically conducting, and a grounding connection for the electrocardiograph being electrically connected to the electrically conducting portion of the tubular member.

3. An electrocardiograph receiver as claimed in claim 1 wherein each of the sponge means is removeably fixed in proximity to the associated electrode by flexible fingers projecting inwardly into the sponge means.

* * * * *